United States Patent [19]

Purdy

[11] 4,025,621

[45] May 24, 1977

[54] METHOD OF CURING AND PROVIDING IMMUNITY FROM VIRAL INFECTIONS

[76] Inventor: Clarence L. Purdy, 7705 Vicar St., New Carrollton, Md. 20784

[22] Filed: Jan. 9, 1975

[21] Appl. No.: 539,923

[52] U.S. Cl. .............................. 424/127; 424/128; 424/151
[51] Int. Cl.² ................ A61K 33/00; A61K 33/42; A61K 33/16
[58] Field of Search .................. 424/127, 128, 151

[56] References Cited

OTHER PUBLICATIONS

Chem. Abst. Subject Index, 8th Collective Edit vol. 66–75, (1967–1971) pp. 4757S–47578S.

*Primary Examiner*—Sam Rosen
*Attorney, Agent, or Firm*—Lane, Aitken, Dunner & Ziems

[57] ABSTRACT

Cure and/or immunity from viral infections of the upper and lower respiratory system is obtained by the administration of minute doses of a water-soluble beryllium salt. The preferred salt is $BeSO_4 \cdot 4H_2O$, which is administered orally in an amount of from about 0.25 to 0.75 milligrams per day.

12 Claims, No Drawings

4,025,621

METHOD OF CURING AND PROVIDING IMMUNITY FROM VIRAL INFECTIONS

BACKGROUND OF THE INVENTION

1. Field of Invention

This invention relates to a method of treating and preventing viral infections of the upper and lower respiratory tract caused by viruses which spread extra-cellulary.

2. Description of the Prior Art

Viruses are infectious agents characterized by their small size and ability to reproduce only within living cells. They are responsible for many diseases in man, including mumps, measles, small pox, yellow fever, poliomyelitis, influenza and the common cold. Viral diseases such as mumps, measles, small pox, yellow fever and poliomyelitis, which were once serious health problems, have been virtually eliminated as a result of the development of specific vacines.

In contrast, no medications have been developed to prevent viral infections of the upper and lower respiratory tract or to eliminate these viruses from the system once a patient has been infected with them. The viruses which cause the respiratory tract infections penetrate the mucus membrane cells of the para-nasal sinuses, nose and throat in order to replicate. This causes cell injury which results in the immediate release of histamine which in turn causes vaso congestion. In order to treat the symptoms of these viral infections, patients are given antihistamines, analgesics and decongestives which make the patient more comfortable, but have no direct effect on the underlying cause of the distress, the virus, and do nothing to activate the patients immunity system, which ultimately destroys and eliminates the virus.

The principal respiratory tract viral infections are the common cold, influenza and pneumonia. They are caused by six groups of viruses, to wit, Rhinoviruses, adenoviruses, respiratory syncytial viruses, influenza viruses, para influenza viruses, and Herpes simplex viruses. These broad groups are composed of over 150 serotypes or strains and all except the Herpes simplex viruses, spread from cell to cell extra-cellularly.

SUMMARY OF THE INVENTION

The principal object of this invention is therefore to provide a method of treating persons infected with, or to immunize persons from infection with, viruses of the upper and lower respiratory tract.

A mor specific object of the invention is to provide a method of activating a persons immune system to destroy and eliminate the viruses of the respiratory tract.

An even more specific object of the invention is to provide a method of activating the bodies immune system to destroy viruses of the respiratory tract which spread extracellularly.

A further specific object of this invention is to provide a method of eliminatng and destroying infections of the upper and lower respiratory tract caused by Rhinoviruses, adenoviruses, respiratory syncytial viruses, influenza viruses and para influenza viruses.

These and other objects are achieved by the administration of a minute dose of a water soluble beryllium salt to a person having an upper respiratory tract viral infection to a person seeking immunity from such an infection.

DESCRIPTION OF THE PREFERRED EMBODIMENTS

Beryllium is a trace element in humans which has no known function. Moreover, beryllium and its salts are considered highly toxic, even in small quantities. However, it has now been found that the administration of water soluble beryllium salts in amounts below toxic quantities, to persons having an upper or lower respiratory tract viral infection, will cure the infection. Moreover, if the same beryllium salt is adminsitered to a patient not having a virus infection it will provide immunity to such infection. Patients treated with oral doses of beryllium salts in accordance with this invention have not suffered any toxic effects or adverse side reactions.

The invention may be used to treat upper and lower respiratory tract infections caused by viruses which spread extra-cellularly. Thus, it has been effective against infections caused by Rhinoviruses, adenoviruses, respiratory syncytial viruses, influenza viruses and para influenza viruses. The Rhinoviruses, which may be subdivided into 60 serotypes are the most common cold causing viruses. The adenoviruses include 39 serotypes, of which types 1, 3 and 5 are the most common cause of upper respiratory tract infection in children. Types 5, 7 and 14 of these viruses are the most common cause of infection in adults. The known influenza viruses include subgroups $A_0$, $A_1$, $A_2$ and $A_3$ and the B viruses. The para influenza viruses include type 1, 2, 3 and 4. It should be understood that this invention is effective against all viruses which spread extra-cellularly and which cause respiratory tract infections, and not just the ones listed above. The beryllium treatment has not been efffective against viruses, such as, Herpes simplex, which do not spread extra-cellularly.

The desired results of this invention can be achieved by administering the beryllium salt either orally or by injection. However, the preferred technique is by oral administration, since local reaction at the point of injection may be objectionable. The beryllium compound may be incorporated in a tablet, food, liquid, or any other non-toxic carrier. The preferred technique is to dissolve the beryllium salt in water.

The beryllium compound may be any water soluble salt of beryllium. These salts include $BeCl_2$, $Be_3(PO_4)_2$, $Be(NO_3)_2$, $BeBr_2$, $BeF_2$, $Be(ClO_4)_2$, $BeSeO_4$ and $BeSO_4$. Preferably $BeSO_4$ is used, most preferably as $BeSO_4 \cdot 4H_2O$.

The beryllium salt should be administered as a daily dosage which will supply a sufficient quantity of beryllium ion to achieve the desired purpose. Using the preferred $BeSO_4 \cdot 4H_2O$ the dosage should be between about 0.25 milligrams and about 0.75 milligrams per day, preferably about 0.5 milligrams per day for an adult. With other salts, the dosage which will supply the same amount of beryllium can be easily calculated by conventional stoichiometric techniques. The amount of the dose will of course depend upon the degree of infection and the size of the patient.

Relief from upper respiratory tract viral infections caused by virus which spread extra-cellularly can be obtained from a single dose of the beryllium salt. However, complete relief was obtained in only ten per cent of the patients when the beryllium was administered only once. Therefore, multiple doses are generally required. While daily administration for from two to seven days will achieve the desired results in most patients, it has been found that in 90 per cent of the patients suffering from an acute cold complete relief is attained in 4 days. Immunity from viral infections can be achieved if the beryllium salt is administered at least two or three times a week.

Twenty patients, randomly selected, suffering from an acute cold of more than one day duration were treated with 0.5 milligrams of $BeSO_4 \cdot 4H_2O$ contained in an aqueous solution, for four consecutive days. Eighteen of these persons were completely recovered at the end of this time. The patients were monitored for two to three months after the treatment and no relapses occurred.

A dose of 0.5 milligrams of $BeSO_4 \cdot 4H_2O$ was orally administered in an aqueous solution to five other patients two or three times a week throughout one winter. Each of these patients had a history of several colds each winter. One of the patients was infected with influenza, the remaining patients were free of colds and flu throughout the winter.

In addition to the above use against colds, beryllium salts have been used successfully against influenza caused by type B viruses and London influenza.

A solution useful for the treatment disclosed may be prepared by dissolving the beryllium salt in water. For example, one gram of $BeSO_4 \cdot 4H_2O$ dissolved in 100 ml of water will provide 100 doses of 0.5 milligrams. One milliliter of this solution can be mixed in a glass of water and the patient will not detect any taste.

Although the fundamental reason for the success of the present invention in curing, and providing immunity from, viral infections of the upper respiratory tract is not understood it is believed that the beryllium ion activates the IgA antibodies, which confine the viruses to the epithelium. Normally when a virus enters the body, type specific antibodies, which destroy the virus, are produced. If the number of viruses is too great the antibodies are overwhelmed and infection occurs. The virus is also attacked by the humoral immune system which contains at least nine enzymes. One of these enzymes is called $C_4$ and is a magnesium metalloenzyme. Since beryllium and magnesium are chemically closely related, it is speculated that beryllium forms a metalloenzyme, which supplements the components of the humoral immune system and activates the natural antibodies which then inactivate the viruses. These antibodies are not believed to be type specific antibodies, which would be formed by the immunity system if no beryllium were administered.

I claim:

1. A method of treating upper and lower respiratory tract viral infections caused by viruses which spread extracellularly comprising administering an effective amount of a water soluble beryllium salt to a subject injected with a viral infection.

2. The method of claim 1 wherein said beryllium salt is administered orally.

3. The method of claim 2 wherein said beryllium salt is $BeCl_2$, $Be_3(PO_4)_2$, $Be(NO_3)_2$, $BeBr_2$, $BeF_2$, $Be(ClO_4)_2$, $BeSeO_4$ and $BeSO_4$.

4. The method of claim 2 wherein said beryllium salt is $BeSO_4 \cdot 4H_2O$.

5. The method of claim 4 wherein said $BeSO_4 \cdot 4H_2O$ is administered in an amount of about 0.25 to 0.75 milligrams per day.

6. The method of claim 5 wherein said $BeSO_4 \cdot 4H_2O$ is administered in an amount of about 0.5 milligrams per day.

7. The method of claim 2 wherein said viral infection is a common cold or influenza.

8. The method of claim 7 wherein said beryllium salt is $BeCl_2$, $Be(PO_4)_2$, $Be(NO_3)_2$, $BeBr_2$, $BeF_2$, $Be(ClO_4)_2$, $BeSeO_4$ and $BeSO_4$.

9. The method of claim 7 wherein said beryllium salt is $BeSO_4 \cdot 4H_2O$.

10. The method of claim 9 wherein said $BeSO_4 \cdot 4H_2O$ is administered in an amount from 0.25 to 0.75 milligrams per day.

11. The method of claim 10 wherein said $BeSO_4 \cdot 4H_2O$ is administered in an amount of about 0.5 milligrams per day.

12. The method of claim 7 wherein said infection is caused by Rhinoviruses, adenoviruses, respiratory syncytial viruses, influenza viruses or para influenza viruses.

* * * * *

UNITED STATES PATENT OFFICE
CERTIFICATE OF CORRECTION

Patent No. 4,025,621　　　　　　　　Dated May 24, 1977

Inventor(s)　　Clarence L. Purdy

It is certified that error appears in the above-identified patent and that said Letters Patent are hereby corrected as shown below:

Column 1, line 52, "mor" should read --more--, line 58, "extracellularly" should read --extra-cellularly--.

Column 2, line 47, "Bef$_2$" should read --BeF$_2$--.

Column 4, line 10, (claim 1) "extracellularly" should read --extra-cellularly--, line 29, (claim 8) "Be(PO$_4$)$_2$" should read --Be$_3$(PO$_4$)$_2$--.

Signed and Sealed this sixteenth Day of August 1977

[SEAL]

Attest:

RUTH C. MASON
Attesting Officer

C. MARSHALL DANN
Commissioner of Patents and Trademarks